United States Patent [19]

Chu

[11] Patent Number: 5,574,135
[45] Date of Patent: *Nov. 12, 1996

[54] PROCESS FOR MAKING VANCOMYCIN

[75] Inventor: Alexander H. T. Chu, Buffalo Grove, Ill.

[73] Assignee: Abbott Laboratories, Abbott Park, Ill.

[*] Notice: The term of this patent shall not extend beyond the expiration date of Pat. No. 5,149,784.

[21] Appl. No.: 387,961

[22] Filed: Feb. 10, 1995

Related U.S. Application Data

[63] Continuation of Ser. No. 128,328, Sep. 28, 1993, abandoned, which is a continuation of Ser. No. 871,610, Apr. 20, 1992, abandoned, which is a continuation of Ser. No. 550,774, Jul. 10, 1990, abandoned.

[51] Int. Cl.$^6$ .............................. C07K 1/14; C07K 9/00
[52] U.S. Cl. ...................... 530/344; 530/317; 530/322
[58] Field of Search ........................... 530/317, 322, 530/344, 323

[56] References Cited

U.S. PATENT DOCUMENTS

| | | | |
|---|---|---|---|
| 3,067,099 | 12/1962 | McCormick et al. | 424/115 |
| 4,440,753 | 4/1984 | McCormick et al. | 424/124 |
| 4,667,024 | 5/1987 | Sitrin et al. | 536/16.9 |
| 4,845,194 | 7/1989 | Glass et al. | 530/344 |
| 5,149,784 | 9/1992 | Chu | 530/344 |

FOREIGN PATENT DOCUMENTS

| | | |
|---|---|---|
| 0241758 | 10/1987 | European Pat. Off. . |
| 0262941 | 4/1988 | European Pat. Off. . |
| 0294990 | 12/1988 | European Pat. Off. . |
| 0303021 | 2/1989 | European Pat. Off. . |
| 0323150 | 7/1989 | European Pat. Off. . |
| 2151234 | 7/1985 | United Kingdom . |

*Primary Examiner*—Christina Y. Chan
*Attorney, Agent, or Firm*—Andreas M. Danckers; Michael J. Ward

[57] ABSTRACT

A process for the manufacture of vancomycin which does not require preparation of a phosphate intermediate. The process consists of passing a vancomycin broth through a suitable adsorbent, followed by passing the vancomycin through a second adsorbent, producing a purified vancomycin. Purified vancomycin is then crystallized from the solution by adding a base solution that imparts a pH of above about 9.0 to about 9.5 to the purified vancomycin. The crystallized vancomycin is separated from the solution, dissolved in solution and recrystallized by adding a base solution which imparts a pH of above about 9.0 to about 9.5 to the dissolved solution. The recrystallized vancomycin is dissolved and titrated with hydrochloric acid. Vancomycin. HCl is then precipitated from the solution using an organic solvent.

5 Claims, 1 Drawing Sheet

PROCESS FOR MAKING VANCOMYCIN

This application is a continuation of U.S. Ser. No. 08/128,328, filed Sep. 28, 1993, now abandoned, which was a continuation of U.S. Ser. No. 07/871,610, filed Apr. 20, 1992 abandoned, which was a continuation of U.S. Ser. No. 07/550,774, filed Jul. 10, 1990, abandoned.

TECHNICAL FIELD

The present invention relates to a process for the manufacture of vancomycin.

BACKGROUND OF THE INVENTION

Vancomycin is used to treat infections of methicillin-resistant staphylococci. Vancomycin is produced by cultivating the bacteria *S. orientalis* in a nutrient culture media.

The vancomycin broth is filtered and added to a column that contains an adsorption resin that decolorizes and desalts the vancomycin. The resin is washed, and the vancomycin eluted with a solvent of low pH, followed by decolorization with carbon.

The vancomycin eluant is then further purified using a single recrystallization step at low pH. The crystallized vancomycin is combined with a strong acid such as hydrochloric acid (HCl), and precipitated in an organic solvent such as acetone to form vancomycin.HCl. This process for the manufacture and purification of vancomycin.HCl is disclosed in U.S. Pat. No. 3,067,099 to McCormick et al.

In another example of a prior art process for the manufacture of vancomycin. HCl, a solvent of 0.1% phosphoric acid ($H_3PO_4$) in a solution of 10% isopropyl alcohol (IPA) is used to elute purified vancomycin from the adsorption column. The vancomycin eluant is then concentrated using reverse osmosis or vacuum evaporation. An aqueous solution that contains approximately 60 g/l of potassium phosphate ($KH_2PO_4$) is added to the concentrated vancomycin solution. The $KH_2PO_4$ causes the vancomycin to crystallize from the solution. The resultant slurry is centrifuged to remove the excess liquid. The vancomycin crystals obtained from centrifugation of the slurry are reslurried in sodium hydroxide (NaOH) to a pH of approximately 4.5 followed by treatment with $KH_2PO_4$ to a pH of approximately 2.0. Vancomycin again crystallizes from the solution. The resulting slurry is centrifuged to separate the crystals from the liquid. The resultant solid is dissolved in water and the mixture is eluted in an ion exchange column to prepare vancomycin hydrochloride.

European Patent Application, Publication No. 0323150, to Catt et al. discloses another method to precipitate vancomycin in a base solution with a pH of about 7.8 to about 9.0. At pH's above about 9.0, the base crystallization disclosed in Catt et al. is unsatisfactory because reduced yields and discolored products result; pH's of 8.0 to 8.5 are preferred.

SUMMARY OF THE INVENTION

The present invention is directed to a process for the manufacture of vancomycin using base crystallization at a pH greater than 9.0. Vancomycin is concentrated and purified by elution with a solvent in a column with a suitable adsorbent therein followed by elution through a second column with another adsorbent which decolorizes and desalts the vancomycin. Base is added to the vancomycin eluant in an amount sufficient to impart a pH of above 9.0 to approximately 9.5 to the resulting solution. The vancomycin crystallizes and precipitates from the solution. The crystals are then separated from the solution.

The crystals are redissolved in acid in an amount sufficient to impart a pH of 3.5 to the dissolved solution. A sufficient amount of base is then added to the dissolved solution to increase the pH of the solution to greater than about 9.0. The base causes the vancomycin to crystallize in the solution. After separating the crystals from the solution, the crystals are dissolved by titration with hydrochloric acid to a pH of 3.25. The acidified, dissolved solution is then concentrated and vancomycin.HCl is precipitated from the solution in an organic solvent.

The vancomycin obtained by the present process is of greater purity than vancomycin produced by other processes. Vancomycin purity achieved by prior art processes typically is about 80±4% in the eluate from the purification column. The crystallization method of the present invention dramatically increases the purity of the vancomycin. The vancomycin purity improves to 86±2% after one crystallization as disclosed herein and to 90±1% after two such crystallizations. If prior art crystallization steps utilizing phosphate crystallization are employed at a pH of about 2.0 to 2.5 the purity of the vancomycin is only 85±2% after two crystallization steps.

In addition, the present process has some important advantages over the prior art. Several time-consuming and expensive steps, such as extra elutions and regenerations of the ion-exchange resin for the conversion to the desired salt, are eliminated by this process. The overall yield is higher than those of prior art processes due to the simplification of the process and lower activity loss during crystallization at a pH above 9.0 to about 9.5.

DETAILED DESCRIPTION OF THE PREFERRED EMBODIMENTS

Figure 1:
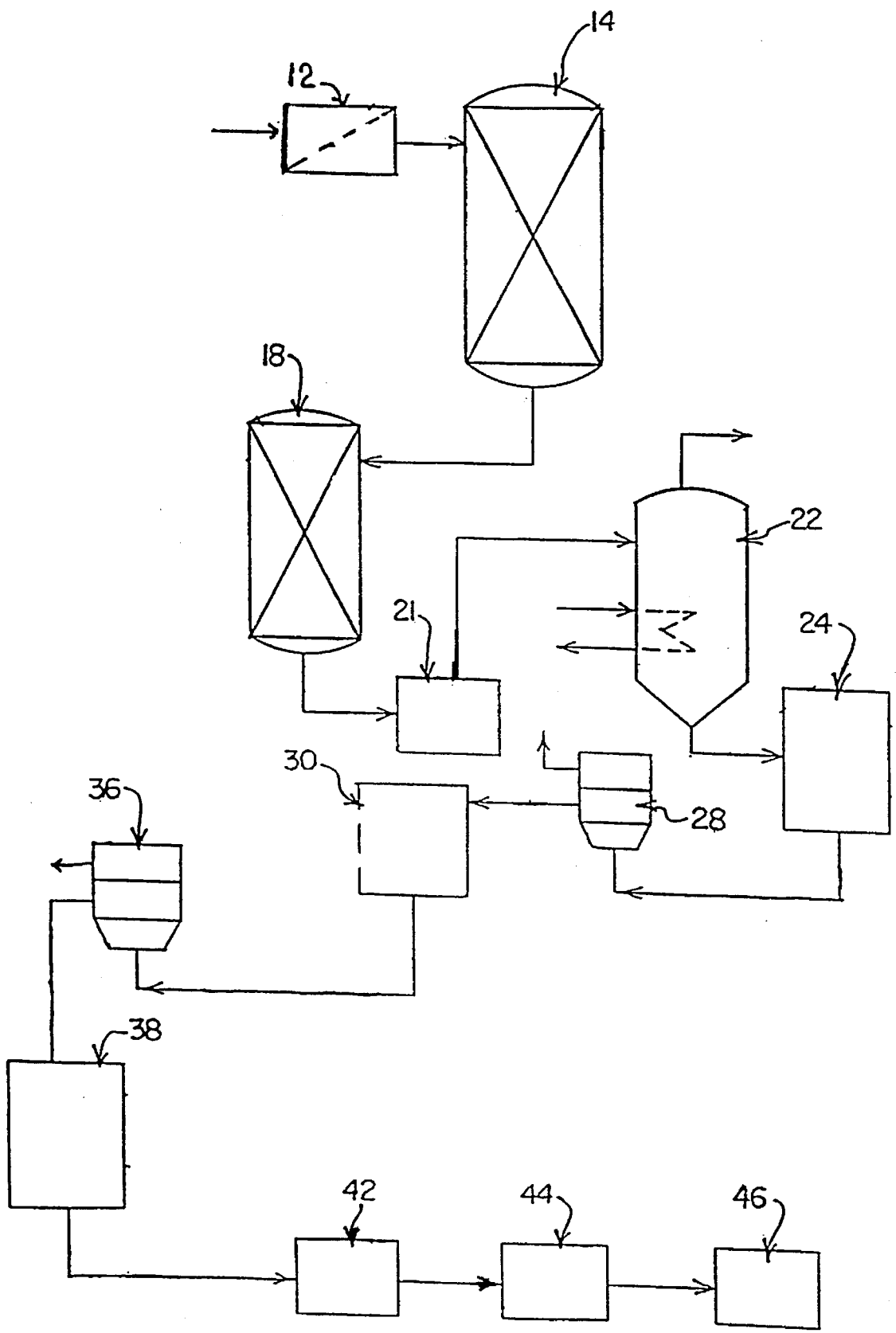
FIG. 1 is a flow diagram of an embodiment of the process disclosed herein.

Vancomycin typically is prepared in a fermentor. Vancomycin broth is then separated and purified. Typically, the desired vancomycin strain is separated from other strains of vancomycin and other impurities by elution of "raw" vancomycin through a column with an adsorbent therein. The preferred strain of vancomycin is vancomycin B. Adsorbents that are selective for vancomycin B such as DOWEX 50 WX2, a cation-exchange resin available from Dow Chemical, and AMBERLITE XAD-16, a non-functional resin available from Rohm & Haas, are utilized to separate other strains of vancomycin and impurities from the vancomycin B.

Elutions are performed in fractions. Each fraction is analyzed to determine the concentration and quantity of vancomycin B therein. In this way the fractions with the greatest concentration of vancomycin B can be combined to optimize the yield from the process. The fractions, for convenience, are expressed as the number of bed or column volumes they represent. The purity of the vancomycin varies from fraction to fraction and depends on a number of factors such as the solvent and the fermentation medium.

Referring to FIG. 1 a vancomycin broth is optionally passed through filter 12 and loaded onto an adsorption column 14 filled with a cation-exchange resin such as DOWEX 50 WX2. The adsorption column 14 is eluted with a base solution of 0.25N $NH_4OH$. The eluant from column 14 is then loaded onto column 18 which is filled with a polymeric adsorption resin such as XAD-16 for desalting and color adsorption. Prior to loading, the XAD-16 resin is sequentially washed with solutions of hydrogen sulfate ($H_2SO_4$) in methanol (MeOH); $H_2SO_4$/MeOH/$H_2O$; a MeOH/$H_2O$ solution; sodium hydroxide solution; and water. The column 18 is eluted with a solvent comprising a C1- to C4 alcohol such as, for example, either 0.1% HCl or 0.2N acetic acid in a solution that is 10% alcohol, such as methanol, ethanol, propanols, butanols, or mixtures thereof in water. The eluant is collected in fractions and analyzed for the presence of vancomycin. B.

The eluant from column 18 is concentrated by reverse osmosis in a module 21. Alternatively, vacuum evaporation can be utilized. The concentrated eluant may be further concentrated to remove alcohol by vacuum evaporation in evaporator 22. The vancomycin is concentrated to approximately 200 g/l.

The pH of the concentrated eluant is reduced to 3.0 by adding a sufficient amount of HCl thereto. The concentrated solution is placed in the vessel 24 to which is added a base solution such as, for example, $NH_4OH$. Sufficient base is added to raise the pH of the concentrated solution to above 9.0 to about 9.5 and form a slurry.

The solids are separated from the slurry in centrifuge 28 and washed with water and/or acetone or methanol to yield a solid of vancomycin free base. In an alternate embodiment, a filter or other liquid/solid separation apparatus can be used. The solid is deposited in vessel 30 where it is dissolved in an acid such as 36 to 38% HCl and crystallized by adding base such as a 28% solution of $NH_4OH$ to vessel 30. The acid is added in an amount sufficient to lower the pH to about 3.5±0.5 to get complete dissolution. The base is added in an amount sufficient for the solution to reach a pH of above 9.0 to about 9.5. Vancomycin crystallizes in the solution. To facilitate crystallization, the solution is chilled until vancomycin crystals are formed. The filtrate from the filter 28 is discarded.

The vancomycin crystals are then separated from the solution in a centrifuge or filter 36 and the resulting filter-cake washed with water and/or acetone or methanol. The resulting solids are placed in vessel 38. Water is added to the vessel 38 to reslurry the solid precipitate and the resultant slurry is titrated with hydrochloric acid. The titration proceeds until the solution reaches a pH of 3.0 to 3.5. The titrated solution is then optionally treated with carbon to remove pyrogens in column 42. The titrated solution is then concentrated by reverse osmosis in module 44 and precipitated in acetone in vessel 46 to produce Vancomycin.HCl.

The present invention will be more readily understood by the following representative examples.

EXAMPLE 1

PREPARATION OF VANCOMYCIN.HCl

Vancomycin.HCl was produced according to a procedure in which the "raw" vancomycin was obtained from eluates of a DOWEX 50 cation-exchange resin column that were diluted after 1.2 to 1.5 bed volumes and passed through a five-pack in-line filter. The diluted eluates were then loaded onto an XAD-16 resin column at a loading capacity of approximately 30 grams of activity per liter of resin. The column was then washed by a 0.2$\underline{N}$ solution of acetic acid and eluted with 0.2$\underline{N}$ acetic acid in an aqueous solution that was 10% alcohol.

The free monovalent acetic acid was diafiltered from the eluted vancomycin in a reverse osmosis unit. Two base crystallizations were then performed on the eluted, concentrated vancomycin by combining the concentrated vancomycin with $NH_4OH$ in an amount sufficient to increase the pH to above 9.0 to about 9.5 for both glycerol (Run #1) and sugar runs (Runs #2 & #3). After the crystals were formed, a centrifuge or a filter was used for liquid/solid separation. Not all samples were carbon treated.

Table I is a summary of the results of product analyses made on the vancomycin.HCl produced by the above procedure.

TABLE I

| Preparation Batch (Feed) | Summary of Examples | | |
|---|---|---|---|
| | 1 Glycerol | 2 Sugar | 3 Sugar |
| Product[3] | | | |
| APHA Color[4] | 150 | 200 | <200 |
| HPLC purity | 89.5% | 90.0% | 89.5% |
| LSI (largest single impurity) | 2.8% | 2.3% | 3.2% |
| pH | 2.98 | 3.0 | 3.1 |
| % $PO_4$ | N.D. | N.D. | N.D. |
| % acetate | N.D. | N.D. | N.A.[1] |
| Moisture | 2.3% | 3.0% | 0.6% |
| % acetone | 0.2% | 1.6% | 2.0% |
| ROI | 0.06% | 0.02% | 0.05% |
| Biopotencies (anhydrous)[6] | 1070 µg/mg | 1040 µg/mg | 1014 µg/mg |
| Pyrogen | pass | N.A.[1] | pass |
| Yield[2] | | | |
| DOWEX50 resin –> HCl | 72% wt | 90% wt | 80% wt |
| HI –> HCl | 65% wt | 81% wt | 72% wt |
| ΣMLS/washes[5] | 20% kgA | 18% kgA | 10% kgA |

TABLE I-continued

Summary of Examples

| Preparation Batch (Feed) | 1 Glycerol | 2 Sugar | 3 Sugar |
|---|---|---|---|
| Mass Balance | 84% kgA | 99% kgA | 82% kgA |

[1] Not tested or carbon treated
[2] Assume 90% step yield of HI (Harvest In) --> DOWEX50 resin
[3] All products meet the Infrared Identity Requirements
[4] American Public Health Association uses a platinum-cobalt standard solution to determine the color of aqueous solution
[5] Sum of activities in mother liquors and washes.
[6] Biopotency (anhydrous) is equal to biopotency (as is) divided by (1-% moisture).

The high pressure liquid chromatography (HPLC) purities of the final products were between 89 and 90%, and the APHA color readings were between 150 and 200. Residual phosphate and acetate levels were essentially non-detectable and the residues on ignition (ROI) were less than 0.1%. Anhydrous biopotencies were all in excess of 1000 µg/mg.

The examples herein illustrate yields of from 65% to 80% by weight, assuming a 90% yield in the step from the harvest from production to the eluate from the DOWEX 50 cation-exchange resin column (the first elution). The loss of vancomycin into solution during base crystallization is limited to about 5 to 20 g/l which is the solubility of vancomycin at a pH of above 9.0 to 9.5.

Though an elution solvent of acetic acid was utilized in the process for purifying the vancomycin.HCl for this example, it has been determined that an elution solvent of 0.1% HCl in 10% alcohol/water solution is also acceptable.

EXAMPLE 2

EFFECT OF pH ON SOLUBILITY

Preparations 4–6 that were prepared by the procedure of Example 1, were used to determine the effect of pH on the crystallization of vancomycin. Prior to the base crystallization step, the pH of the solution must be optimized to maximize the efficiency of the crystallization. Table II shows the effect of pH on vancomycin crystallization.

TABLE II

Effect of pH on Vancomycin Crystallization

| Preparation | 4 | 5 | 6 |
|---|---|---|---|
| pH | 7.5 | 8.5 | 9.5 |
| Solubility | 25 g/l | 3.4 g/l | 20 g/l |
| Stability | −0.12%/day | −0.14%/day | −0.23%/day |
| Color removal | least | some | good |
| Crystal size | | | |
| (t = 0) | large (>20µ) | small (~5µ) | No crystallization |
| (t = 16 h) | — | median (~20µ) | median (~20µ) |

Reducing the solubility of vancomycin minimizes the loss of vancomycin into solution. Table II indicates that, at a pH of 8.5 the vancomycin has the preferred lower solubility. Unfortunately, at this pH, color separation is unsatisfactory because of the co-crystallization of color bodies with vancomycin. Table II illustrates that satisfactory color removal can be obtained at a pH of 9.5, but the process takes 16 hours as opposed to the instantaneous crystallization that is obtained at lower pH's. Although Table II indicates the stability of the crystals obtained at the higher pH is somewhat less than the stability of crystals obtained from a lower pH, that difference has been determined to be insignificant.

EXAMPLE 3

PROCESS FOR MAKING VANCOMYCIN.HCl

Approximately 800 liters of the eluate from a DOWEX 50 cation-exchange resin column is removed therefrom after about 1.2 to about 1.5 bed volumes of pre-elution is performed on the column. The eluate is then passed through a 5-pack in-line filter and deposited into an 800-liter sanitary tank. A composite sample is taken for in-process high pressure liquid chromatography (HPLC). The eluant is about fifteen percent solids.

Approximately 100 liters of spent XAD-16 resin is obtained and placed in a screened sanitary tank. The resin is then sequentially regenerated with approximately 50 liters of a 1N solution of hydrogen sulfate ($H_2SO_4$) in methanol (MeOH), 100 liters of 1N $H_2SO_4$ in a solution of 50% MeOH/distilled water, 50 liters of 50% MeOH/water, 300 liters of 1N sodium hydroxide (NaOH), and at least 300 liters of distilled water at a flow rate of 2.5 l/min.

Based on analysis using an HPLC assay, 30–60 g/l of vancomycin is loaded onto the 100 liters of the regenerated resin using crossed flow distribution at a flow rate of 2.5 l/min. The spent load is collected and sampled.

The resin is subsequently washed with 100 liters of 0.2 N acetic acid by flowing the acid downward The cross flow distributor is used at a flow rate of 2 l/min. The spent wash is subsequently collected and sampled.

A 700 liter solution of 10% ethanol/0.2N acetic acid/water is prepared by combining 70 liters of alcohol, 18.1 liters of acetic acid and 611.9 liters water. Vancomycin is eluted from the washed resin with this solution at a rate of 2.5 l/min. Fractions of 100 liters each are collected in sani-tanks. Each fraction is sampled for pH, HPLC and thin layer chromatography (TLC). The activity of each fraction is also determined by TLC. The fractions containing activity are then combined.

The combined solutions are then concentrated to an approximate volume of 60 liters using a reverse osmosis unit. The solution is then diafiltered with at least 300 liters of distilled water to ensure that no free acetic acid remains in the retentate. The retentate is then flushed using a minimum amount of distilled water. The residual ethanol is stripped out of the retentate using a Turba Film Evaporator (TFE) vacuum, which is cleaned prior to use. The unit is operated under full vacuum with a concentrate temperature of less than 25° C. (77° F.). The concentration of the product solids is approximately twenty percent.

The pH of the concentrate is then reduced to approximately 3.0 by adding a solution of 36 to 38% HCl.

The pH of the concentrate is increased to above 9.0 to about 9.5 by adding a 28% solution of $NH_4OH$ in a mixing tank and fully dissolving the vancomycin crystals therein. The solution is stored at 0°–10 C. overnight to crystallize the vancomycin in the solution.

The resulting slurry is centrifuged in a TOLHURST centrifuge until the resultant solid is substantially separated from the liquid. The solid is then washed with 10 liters of distilled water until the cake is substantially free from residual color. The mother liquor and the wash are both sampled, and the volumes recorded. The pH and color of the samples is recorded as well. The wet filtercake is then weighed.

The filtercake is mixed with a volume of distilled water to provide a concentration of 200 grams of product per liter. The mixture forms a slurry. The pH of the resulting slurry is reduced to approximately 3.0–4.0 using an HCl solution with an approximate concentration of 36 to 38% HCl for complete dissolution.

The pH of the slurry is increased to above 9.0 to about 9.5 by adding an $NH_4OH$/water solution with an approximate 28% concentration of $NH_4OH$ in a mixing tank. The dissolved solution is then placed into a cold room overnight to crystallize.

The slurry is centrifuged in a TOLHURST centrifuge until the cake was "dry". The mother liquor and wash were sampled and the volumes, pH's and color of the samples were recorded. The solid product vancomycin base was subsequently weighed.

The solid product is then reslurried in an aliquot of water sufficient to provide a concentration of 125 g of product per liter. The pH of the dissolved solution is then reduced to about 3.25±0.25 by adding a solution with a 36 to 38 percent concentration of HCl in water. The percent solids in the resultant solution is then measured.

Approximately three weight percent of DARCOG-60 activated charcoal, manufactured by ICI, is added to the concentrate. The slurry is mixed well for approximately two hours at a temperature that is less than 25° C. (77° F.) to depyrogenate the solution.

The slurry is then transferred into a pressure vessel which is connected to a Pall 0.2 μmicrofilter. Nitrogen is used to pressurize the slurry through the filter to a receiver that is previously cleaned with sterile water.

The filtered, depyrogenated solution is then concentrated by using reverse osmosis. The concentration of the solids in the solution is approximately twenty-five percent.

The solids are precipitated from the slurry by mixing 5 volumes of acetone per one volume of slurry with the slurry. The precipitate is then centrifuged using a TOLHURST centrifuge followed by approximately 10 liters of an acetone wash.

The resulting solids are then dried using a Divine vacuum tray dryer/under vacuum at 50° C. (120° F.) overnight. The product is covered to avoid contamination.

EXAMPLE 4

EFFECT OF XAD-16 LOADING ON COLOR SEPARATION

Color separation was evaluated as a function of the loading of vancomycin onto the XAD-16 resin column (the second purifying column).

A vancomycin solution purified by elution in DOWEX 50 resin was loaded onto a 20 liter XAD-16 resin column at various loadings. The color analysis performed on the eluants from this column, summarized in Table III below, indicates that loadings of less than 40 grams of activity per liter of resin are necessary to achieve adequate color removal from the final product.

For these preparations, the pH of the vancomycin slurry was adjusted to about 9.1±0.1 using a 28% solution of $NH_4OH$. Two base crystallizations were performed. Excess ammonia was removed by vacuum evaporation before dissolving the resultant slurry in a solution of pH 3.5 which was followed by carbon treatment and acetone precipitation.

TABLE III

| Preparation | 7 | 8 | 9 | 10 | 11 |
|---|---|---|---|---|---|
| Loading | 30 g/l | 70 g/l | 51 g/l | 51 g/l | 40 g/l |
| APHA Color | 200 | <350* | 300 | <350 | 150 |
| HPLC purity | 89.5% | 91.2% | 88.9% | 90.0% | 91.9% |
| LSI impurity | 1.2% | 1.2% | 1.4% | 1.3% | 1.1% |
| Biopotency (anhy) μg/mg | 1018 | 1053 | 1038 | 1056 | 1670 |

*APHA reduced to 250 after a third crystallization.

EXAMPLE 5

PREPARATION OF VANCOMYCIN BASE

Vancomycin base was produced according to a procedure in which the "raw" vancomycin was obtained from eluates of a DOWEX 50 cation-exchange resin column that were diluted after 1.2 to 1.5 bed volumes and passed through a five-pack in-line filter. The diluted eluates were then loaded onto an XAD-16 resin column at various loadings from 30 to 50 grams of activity per liter of resin. The column was then washed by a 0.2N solution of acetic acid and eluted with 0.2N acetic acid in an aqueous solution that was 10% alcohol.

The free monovalent acetic acid was diafiltered from the eluted vancomycin in a reverse osmosis unit. Two base crystallizations were then performed on the eluted, concentrated vancomycin by combining the concentrated vancomycin with $NH_4OH$ in an amount sufficient to increase the pH to above 9.0 to about 9.5. After the formation of base crystals, a centrifuge or a filter was used for liquid/solid separation. An aqueous HCl solution was added to dissolve vancomycin base at pH 3.0–4.0 before recrystallization with $NH_4OH$ at a pH above 9.0 to about 9.5. The centrifuge or filter cake was dried under vacuum at room temperature.

Table IV is a summary of the results of product analyses made on the vancomycin base produced by the above procedure.

TABLE IV

| | Summary of Examples | | |
|---|---|---|---|
| Preparation | 12 | 13 | 14 |
| Loading (XAD-16 resin) | 51 g/l | 30/g/l | 42 g/l |
| HPLC purity | 88.1% | 89.0% | 89.5% |
| Largest Single Impurity | 1.2% | 1.0% | 1.4% |
| pH | 9.1 | 9.2 | 9.1 |
| Moisture | 3.0% | 13.6% | 3.0% |
| Biopotency (as is) | 1027 μg/mg | 986 μg/mg | 1067 μg/mg |

No discoloration was apparent for the vancomycin base solids at this pH range. A slow decrease in the HPLC purity of approximately 3% in the first month was observed for the products stored at room temperature.

The foregoing examples are intended as illustrations only and not intended to limit the invention in any way except in the spirit and scope of the appended claims.

We claim:

1. A process for the manufacture of crystalline vancomycin without causing discoloration thereof comprising:

a) passing a vancomycin broth through a first adsorbent;

b) passing the vancomycin broth produced by step a) through a second adsorbent;

c) adding a solution of base to the product of step b) to produce a solution having a pH of above 9.0 to about 9.5;

d) crystallizing vancomycin base from the solution of step c);

e) substantially separating the crystals from the solution;

f) dissolving the crystallized vancomycin from step e) in an acid solution to produce a solution with a pH of about 3.0 to about 3.5;

g) adding to the solution of step f) a base solution in an amount sufficient to increase the pH of the solution to above 9.0 to about 9.5 to recrystallize the vancomycin base; and h) substantially separating vancomycin base crystals from the solution.

2. The process of claim 1 wherein the vancomycin is eluted through the first adsorbent with a base solvent.

3. The process of claim 1 wherein the vancomycin is eluted through the second adsorbent with a solvent of acid in a water/alcohol solution, said solution comprising a C1- to -C4 alcohol.

4. The process of claim 1 further comprising the step of concentrating the vancomycin solution prior to step c).

5. The process of claim 1 that further comprises the steps of redissolving the recrystallized vancomycin base obtained from step (h) of claim 1 in water, titrating the resulting solution with hydrochloric acid to a pH of about 3.25, concentrating the titrated solution by reverse osmosis, and precipitating vancomyin. HCl from the concentrated solution by the addition of acetone.

* * * * *